United States Patent [19]

Nishimura et al.

[11] 3,994,942

[45] Nov. 30, 1976

[54] METHOD FOR PURIFYING 11-CYANO-UNDECANOIC ACID

[75] Inventors: Kenji Nishimura; Shinichi Furusaki; Kazuo Kuniyoshi, all of Ube, Japan

[73] Assignee: UBE Industries, Ltd., Ube, Japan

[22] Filed: Jan. 23, 1975

[21] Appl. No.: 543,525

[30] Foreign Application Priority Data
Feb. 8, 1974 Japan.............................. 49-15380

[52] U.S. Cl................................ 260/404; 260/404.5
[51] Int. Cl.² ................... C07C 101/04; C11B 3/00
[58] Field of Search ......................... 260/404, 404.5

[56] References Cited
UNITED STATES PATENTS
2,862,940   12/1958   Otsuki et al. ....................... 260/404

3,217,027   11/1965   Little ............................... 260/404 X

FOREIGN PATENTS OR APPLICATIONS
894,720   4/1962   United Kingdom ................. 260/404

Primary Examiner—Patrick P. Garvin

[57] ABSTRACT

11-cyano-undecanoic acid having a high purity of 99% or more is obtained by the steps of dissolving a crude 11-cyano-undecanoic acid in the form of free acid or its ammonium salt into a mixture solvent consisting of acetic acid or propionic acid and water in a mixing ratio by weight of 1 : 0.05 to 3; bringing a refining gas containing therein ozone into contact with said solution in order to decompose impurities, especially, coloring substances in said solution, and; crystallizing and separating the purified 11-cyano-undecanoic acid from said solution.

8 Claims, 2 Drawing Figures

METHOD FOR PURIFYING 11-CYANO-UNDECANOIC ACID

The present invention relates to a method for purifying 11-cyano-undecanoic acid, and more particularly, relates to a method for purifying 11-cyano-undecanoic acid from a crude 11-cyano-undecanoic acid containing therein colored substances as impurities.

11-cyano-undecanoic acid is useful as an intermediate material for producing polymeric materials. For example, 11-cyano-undecanoic acid is converted to 12-amino-dodecanoic acid by hydrogenation. The 12-amino-dodecanoic acid is polymerized to produce Nylon 12.

British Pat. No. 1,198,422 discloses a method for producing 11-cyano-undecanoic acid by thermally decomposing 1, 1'-peroxy-dicyclohexylamine at a high temperature of 300° to 1000° C. German Patent Application Laying-open No. 2,038,956 discloses an improved method for producing 11-cyano-undecanoic acid by the introduction of an inert gas into the decomposition system.

The thermal decomposition product obtained by these methods contains besides 11-cyano-undecanoic acid in an amount corresponding to 50 to 60% of the weight of the 1, 1'-peroxy-dicyclohexyamine, $\epsilon$-caprolactam in an amount corresponding to 10 to 20% thereof, cyclohexanone in an amount corresponding to 10 to 20% thereof and other by-products (including saturated and unsaturated carboxylic acids, nitriles and cyclic imides) in an amount corresponding to 10 to 20% thereof. Generally, the thermal cracking product is dark brown or brownish black. Accordingly, in order to obtain 11-cyano-undecanoic acid usable as a material for the polymer industry, it is required that 11-cyano-undecanoic acid having impurities and colored substances in an amount as small as possible be isolated with a high recovery yield from the thermal cracking product.

British Pat. No. 1,289,680 discloses a method for recovering and refining 11-cyano-undecanoic acid from the thermal decomposition product. In the British patent method, the thermal decomposition product is subjected to distillation, in order to concentrate 11-cyano-undecanoic acid and distill away cyclohexanone and other impurities having a relatively low boiling point, and the resultant crude 11-cyano-undecanoic acid is sprayed into water in order to eliminate $\epsilon$-caprolactam and other water-soluble impurities. However, the British patent method can merely eliminate a minor portion of the impurities from the crude 11-cyano-undecanoic acid and has substantially no effect for eliminating the coloring substances from the 11-cyano-undecanoic acid.

Also, British Pat. No. 1,266,213 discloses a method for isolating 11-cyano-undecanoic acid by dissolving the crude 11-cyano-undecanoic acid in a solvent containing therein ammonia, for example, aqueous ammonia solution, crystallizing the ammonium salt from the solvent by cooling and, then, separating the crystallized ammonium salt from the solvent.

This method can recover an ammonium salt of 11-cyano-undecanoic acid having relatively high purity. However, the aqueous ammonia solution has a relatively high solubility to the 11-cyano-undecanoic acid or its ammonium salt at a temperature higher than 20° C. Accordingly, in order to crystallize a refined ammonium salt of 11-cyano-undecanoic acid having a high yield, it is necessary that the solution be cooled to a temperature of 10° C or lower. This results in an undesirable economic disadvantage. The British patent method further includes the disadvantage that the resultant crystallized 11-cyano-undecanoic acid still contains some amount of unknown colored substances which are difficult to eliminate from the crude 11-cyano-undecanoic acid by way of recrystallization from the solvent consisting of aqueous ammonia solution.

In Ser. No. 543,445, we proposed a method for isolating 11-cyano-undecanoic acid in the form of its ammonium salt from the thermal cracking product by bringing ammonia gas into contact with a solution of the thermal cracking product in a solvent consisting of an aromatic hydrocarbon having 6 to 8 carbon atoms, then, separating the crystallized ammonium salt from the solution. According to the above-mentioned method, an ammonium salt of 11-cyano-undecanoic acid having a high purity of 99% or more can be obtained in a recovery yield of 95% by weight or more. However, the method also failed to completely remove the colored substances from 11-cyano-undecanoic acid.

Accordingly, in order to obtain high purity colorless 11-cyano-undecanoic acid or its ammonium salt directly usable in the polymer industry, it is necessary that the 11-cyano-undecanoic acid or its ammonium salt isolated by the conventional methods described herein-before be further purified by way of recrystallizings repeated twice or more. However, the repeated recrystallizing results in an operational complexity and economic disadvantages.

The object of the present invention is to provide a method for purifying 11-cyano-undecanoic acid in the form of free acid or its ammonium salt by eliminating colored substances therefrom in order to obtain high purity colorless 11-cyano-undecanoic acid with a high yield.

The above-stated objects can be accomplished by the method of the present invention, which method comprises the steps of:
preparing a solution of a crude 11-cyano-undecanoic acid in the form of free acid or its ammonium salt in a mixture solvent consisting of acetic acid or propionic acid and water in a mixing ratio by weight of 1 : 0.05 to 3;
bringing a refining gas containing therein ozone into contact with said solution;
crystallizing said 11-cyano-undecanoic acid from said mixture solvent, and;
separating said crystallized 11-cyano-undecanoic acid from said solution.

The method of the present invention is based on the discovery that the colored substances contained in the crude 11-cyano-undecanoic acid can be easily decomposed by the action of ozone, but the 11-cyano-undecanoic acid itself is extremely resistive against the action of ozone under the ozone treating conditions. It is surprising that, in the method of the present invention, the ozone selectively attacks only the colored substances in the crude 11-cyano-undecanoic acid but does not decompose the 11-cyano-undecanoic acid itself. If another oxydizing agent, for example, potassium permanganate, is used, not only the impurities and coloring substances but the 11-cyano-undecanoic acid itself are decomposed by the oxidizing action thereof. This result is economically disadvantageous.

Further, we have discovered that a solvent mixture consisting of acetic acid or propionic acid and water is excellent as a solvent for the crystallization of 11-cyano-undecanoic acid having a high yield. That is, it was discovered that the mixture solvent consisting of acetic acid or propionic acid and water is more advantageous than other solvents, for example, diluted aqueous ammonia solution, water-containing alcohol, and water-containing chloroform, for the following reasons.

a. High non-reactivity to ozone.
 b. High enough solubility to completely dissolve 11-cyano-undecanoic acid therein at a high temperature and high enough insolubility to completely crystallize 11-cyano-undecanoic acid at room temperature.
 c. High density and large size of crystals produced therefrom. These properties of the crystals result in easy handling of the slurry wherein the crystals are suspended and in easy separation of the crystals from the solvent by way of filtering or centrifugalizing.
 d. And, finally, excellent dissolving property for the impurities.

Accordingly, highly purified colorless 11-cyano-undecanoic acid can be produced with a high recovery yield by dissolving the crude 11-cyano-undecanoic acid in the form of free acid or its ammonium salt into a mixture solvent consisting of acetic acid or propionic acid and water, bringing a refining gas containing ozone therein into contact with the solution to decompose the impurities, especially, coloring substances, crystallizing the purified 11-cyano-undecanoic acid and separating the crystallized 11-cyano-undecanoic acid.

The method of the present invention can be applied to a crude 11-cyano-undecanoic acid recovered from a crude oily material produced by thermally decomposing 1,1'-peroxy-dicyclohexylamine at a temperature of 300° to 1000° C. The crude oily material can be obtained by separating an oily layer containing 11-cyano-undecanoic acid from the thermal decomposing product. The process of recovery of the crude 11-cyano-undecanoic acid is not critical to the present invention. For example, the crude 11-cyano-undecanoic acid can be recovered from the crude oily material or the thermal decomposition product containing the oily layer by distilling cyclohexanone and other impurities having a low boiling point.

However, in order to reduce wasteful consumption of ozone, it is preferable that the crude 11-cyano-undecanoic acid to be refined by the method of the present invention should have a 2% solution Hazen number of at most 3,000, more preferably, at most 1,000. If the crude 11-cyano-undecanoic acid is remarkably discolored by a relatively large amount of the colored substances, it is preferable that the crude 11-cyano-undecanoic acid be preliminarily refined. The preliminary refining may be effected by way of recrystallizing the 11-cyano-undecanoic acid from a proper solvent or bringing it into contact with activated carbon. It is particularly suitable to start the method of the present invention with the 11-cyano-undecanoic acid semi-refined by the method of our copending U.S. application Ser. No. 543,445, filed Jan. 23, 1975, in which a crude oily material containing 11-cyano-undecanoic acid therein is dissolved in a solvent consisting of an aromatic hydrocarbon having 6 to 8 carbon atoms, ammonia gas is brought into contact with the solution to convert 11-cyano-undecanoic acid to its ammonium salt, which is immediately crystallized from the solution, and the crystallized ammonium salt is separated from the solution. However, the crude 11-cyano-undecanoic acid or its ammonium salt recovered by another method, for example, the methods disclosed in British Pat. Nos. 1,289,680 and 1,266,213 may be used.

In the method of the present invention, when the ammonium salt of the crude 11-cyano-undecanoic acid is used as the starting material, it may be preliminarily converted into the form of free acid by treatment with a diluted aqueous solution of a mineral acid, for example, hydrochloric acid or sulfuric acid. In the conversion, there is no loss of the 11-cyano-undecanoic acid, because 11-cyano-undecanoic acid in the form of free acid has no substantial solubility in the aqueous solution of the mineral acid. However, the ammonium salt of 11-cyano-undecanoic acid can be directly subjected to the method of the present invention without conversion, because the ammonium salt is naturally converted to the free acid when dissolved in the mixture solvent of the present invention containing acetic acid or propionic acid.

In the method of the present invention, the mixture solvent for the crude 11-cyano-undecanoic acid consists of acetic acid or propionic acid and water mixed with each other in a mix ratio by weight of 1 : 0.05 to 3, preferably, 1 : 0.5 to 2. If water is mixed with acetic acid or propionic acid in a mix ratio by weight of more than 3, the resultant solvent has too low a solubility for 11-cyano-undecanoic acid. Even if the mixture solvent can completely dissolve 11-cyano-undecanoic acid therein at a high temperature, the solution undesirably tends to be separated into two layers having different compositions from each other while the high temperature solution is cooled to a low temperature. Also, if water is mixed with acetic acid or propionic acid in a mixing ratio by weight of less than 0.05, the resultant mixture solvent has too high a solubility for 11-cyano-undecanoic acid at about room temperature. This high solubility results in incomplete crystallization of the purified 11-cyano-undecanoic acid from the solvent mixture. This is an economic disadvantage.

The concentration of the 11-cyano-undecanoic acid in the mixture solvent is determined in response to the type of the organic acid to be mixed with water and mixing ratio of the organic acid to water. For example, if the solvent mixture contains water in a relatively high proportion, the solubility of the solvent mixture for 11-cyano-undecanoic acid is relatively low. When a large amount of 11-cyano-undecanoic acid is mixed into this type of solvent mixture, even if a uniform solution can be obtained by heating the mixture to a high temperature, when cooled the uniform solution is separated into two layers having different compositions from each other and 11-cyano-undecanoic acid in the two layers is separately crystallized from the layers.

The preferable concentration of 11-cyano-undecanoic acid in the solvent mixture will be explained in detail hereinafter by referring to the accompanying drawings, in which.

Figure 1:
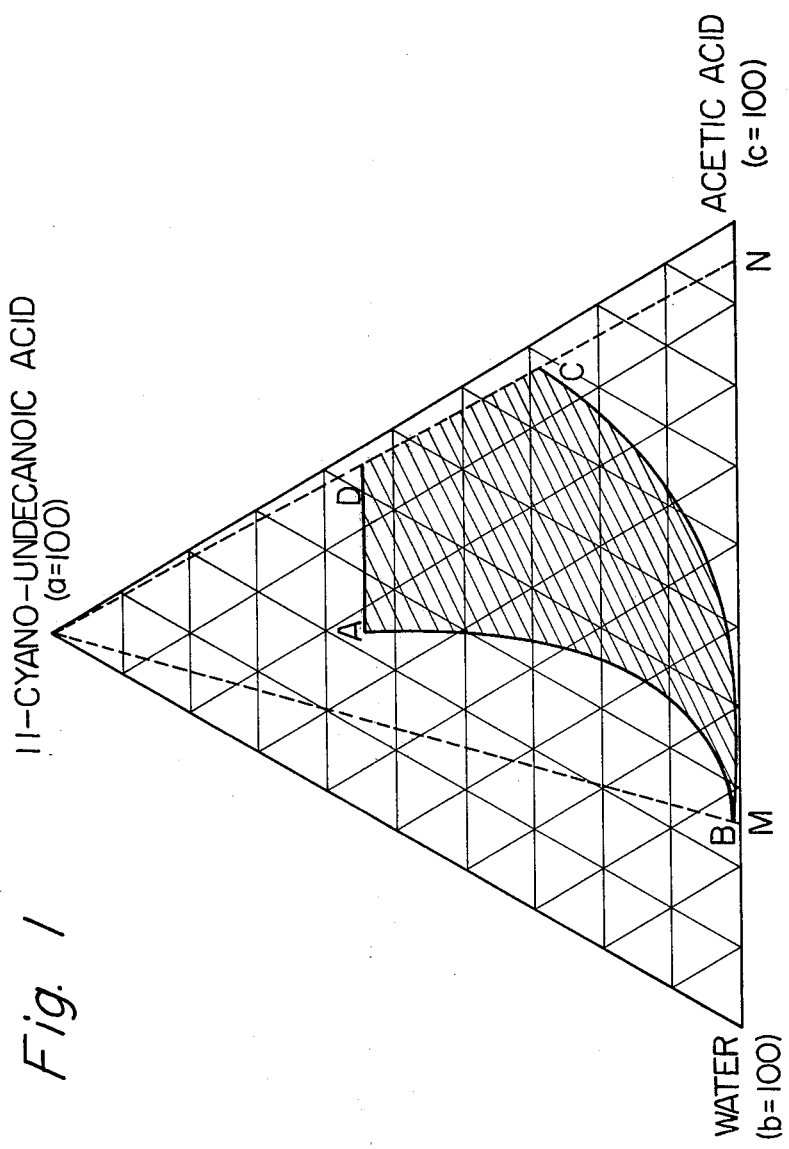
FIG. 1 is a triangular coordinate system showing a preferable concentration range of 11-cyano-undecanoic acid to be dissolved in a solvent mixture consisting of acetic acid and water.

Referring to FIG. 1, showing a triangular coordinate system having three ordinates respectively presenting the weight percentage of 11-cyano-undecanoic acid, water and acetic acid, the 11-cyano-undecanoic acid in the form of free acid or its ammonium salt, water and acetic acid are mixed in a ratio of $a : b : c$. In the solvent mixture usable for the method of the present invention, the proportion of water to acetic acid $b : c$ is on a line defined by coordinates $M(a=0, b=75$ and $c=25)$ and $N(a=0, b=5$ and $c=95)$. In the preparation of the solution of the crude 11-cyano-undecanoic acid in the solvent mixture, it is preferable that the proportion $a : b : c$ is on or within a figure defined in FIG. 1 by coordinates $A(a=55, b=25$ and $c=25)$, $B(a=1, b=74$ and $c=25)$, $C(a=29, b=3$ and $c=68)$ and $D(a=55, b=2$ and $c=43)$. Curve AB shows a preferable limit line in the proportions of water and 11-cyano-undecanoic acid to acetic acid. Curve BC corresponds to a solubility curve of 11-cyano-undecanoic acid, in the solvent mixture consisting of water and acetic acid at about room temperature.

Figure 2:
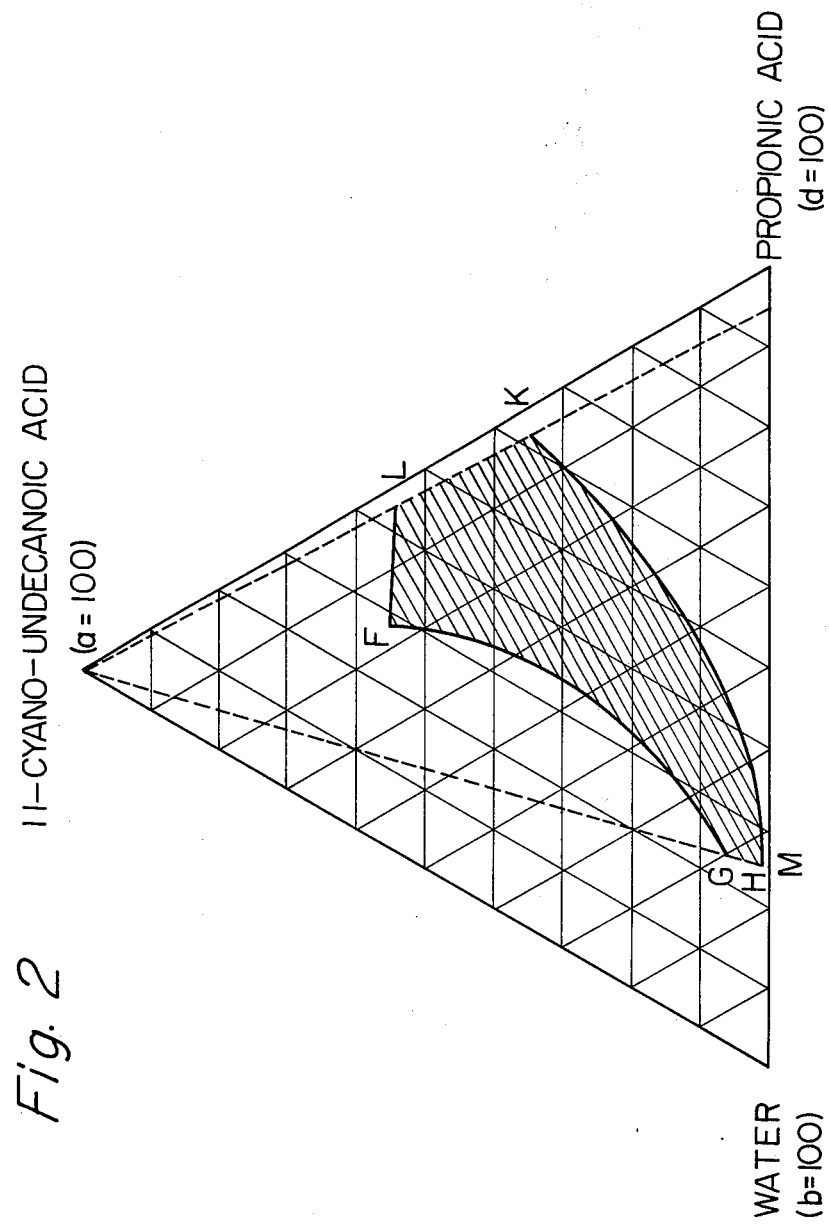
FIG. 2 is another triangular coordinate system showing a preferable concentration range of 11-cyanoundecanoic acid to be dissolved in the other solvent mixture consisting of propionic acid and water.

Referring to FIG. 2, indicating a triangular coordinate system having three ordinates respectively presenting the weight percentage of 11-cyano-undecanoic acid, water and propionic acid, the 11-cyano-undecanoic acid in the form of free acid or its ammonium salt, water and propionic acid are mixed in a ratio of $a : b : d$. In the preparation of the solution of the crude 11-cyano-undecanoic acid in the solvent mixture, it is preferable that the proportion $a : b : d$ is on or within a figure defined in FIG. 2 by coordinates $F(a=55, b=17$ and $d=28)$, $G(a=6, b=70$ and $d=24)$, $H(a=1, b=74$ and $d=25)$, $K(a=35, b=3$ and $d=62)$ and $L(a=55, b=2$ and $d=43)$. Curve FGH shows a preferable limit line on which or on the right side of which: 11-cyano-undecanoic acid and water are beneficially dissolved in propionic acid. Curve HK corresponds to a solubility curve of 11-cyano-undecanoic acid in the solvent mixture consisting of water and acetic acid at about room temperature.

In the case where the crude material containing ammonium salt of 11-cyano-undecanoic acid is directly dissolved in the solvent mixture, the solvent mixture should contain acetic acid or propionic acid in an amount of the sum of the desired amount as a component of the mixture solvent and an amount required for converting the ammonium salt to free acid.

The crude 11-cyano-undecanoic acid in the form of free acid or its ammonium salt is mixed and uniformly dissolved into the solvent mixture by heating to a proper temperature. After the solution is adjusted to a temperature in a proper range, the refining gas is brought into contact with the solution.

The contact of the refining gas with the solution of the crude 11-cyano-undecanoic acid can be made by any of the conventional methods as long as the contact is tightly maintained. For example, the refining gas is directly blown into the solution while the solution is stirred. In another method, the refining gas is brought into contact with the solution which is flowed through any type of gas absorber, for example a bubble column in the same or opposite direction with respect to that of the refining gas.

The refining gas containing ozone therein usable for the method of the present invention may be prepared by any of the conventional processes. Generally, the refining gas preferably contains 0.1 to 5% by volume of ozone therein and is prepared by feeding oxygen gas or air into an ozone generator. However, other refining gases containing ozone in a content ranging outside of the above-mentioned content range or containing ozone together with an inert gas other than air or oxygen gas, can also be utilized for the method of the present invention.

In the method of the present invention, the refining gas containing ozone is brought into contact with the solution of the crude 11-cyano-undecanoic acid at a temperature between 15° and 100° C, more preferably, 15° and 60° C. If the contact is carried out at a temperature higher than 100° C, a large amount of the ozone is lost by the decomposition of the ozone itself. This is an economic disadvantage. The refining operation, if conducted at a temperature lower than 0° C, has no advantages.

The ozone is preferably used in an amount of 0.05 to 5%, based on the weight of the crude 11-cyano-undecanoic acid, in response to the amount of the impurities and colored substances in the solution and contact efficiency of the refining gas with the solution. It is easily determined by observing the change in color of the solution whether or not the amount of ozone used in the refining process is sufficient. That is, the refining gas containing ozone is introduced into the solution until the solution becomes colorless. Since the 11-cyano-undecanoic acid itself does not substantially react with ozone under the treating conditions, there is no limitation in the contact time period of ozone with the solution.

If the crude 11-cyano-undecanoic acid contains a large amount of colored substances therein and a large amount of ozone is necessary for completing refining, it is preferable that the crude 11-cyano-undecanoic acid solution be preliminarily refined by bringing it into contact with activated carbon to remove a portion of the colored substances. However, it is one of the characteristic features of the present invention that some types of colored substances, which cannot be eliminated by the activated carbon, can be easily and rapidly removed from the crude 11-cyano-undecanoic acid solution by the action of ozone in accordance with the method of the present invention. This will be illustrated in Example 2 hereinafter.

By cooling the solution refined by ozone in accordance with the above-mentioned method, the 11-cyano-undecanoic acid is immediately crystallized in the form of colorless crystals having a large size effective for easily separating the crystals from the solution. The temperature for cooling the refined solution is in a range between 5 and 25° C. Generally, when the solution is cooled to an ambient temperature, that is, room temperature, the purified 11-cyano-undecanoic acid can be crystallized in a sufficiently high recovery yield. If it is desired, the crystallization may be carried out at a temperature higher or lower than the ambient temperature.

The crystallized 11-cyano-undecanoic acid in the form of free acid can be separated from the solution by any of the conventional separating methods, for example, filtering and centrifuge. After complete separation, the crystals of the purified 11-cyano-undecanoic acid are beneficially washed with water to remove the solvent mixture. The washing can be effected by using an amount of water sufficient to completely remove the solvent mixture, because the 11-cyano-undecanoic acid is substantially insoluble in water.

According to the method of the present invention the impurities and colored substances in the crude 11-cyano-undecanoic acid which can not be eliminated by a conventional refining agent, for example, activated carbon, or by a conventional refining method, for example, recrystallization from a proper solvent, can be easily and rapidly eliminated, and substantially colorless 11-cyano-undecanoic acid having a high purity of 99.5% or more can be obtained with a high recovery yield.

The features and advantages of the present invention are further illustrated by the examples set forth below, which are not intended to limit the scope of the present invention.

In the examples, the Hazen number of the solution of 11-cyano-undecanoic acid or its ammonium salt was determined by the following method.

A standard Hazen solution was prepared by dissolving 1.246 g of potassium chloroplatinate (containing 500 mg of platinum therein) and 100 g of cobalt chloride hexahydrate into 100 ml of concentrated hydrochloric acid and adjusting the solution to a volume of 1000 ml by adding water. The standard Hazen solution has a Hazen number of 500. For example, a diluted Hazen solution which has been prepared by diluting the standard Hazen solution with water to a volume of ten times that of the original standard Hazen solution, has a Hazen number of 50. The standard Hazen solution has an absorbance of 0.674 to a visible ray at 457 m$\mu$ when measured using an optical glass cell having a 5 cm thickness.

A 2% solution of 11-cyano-undecanoic acid or its ammonium salt was prepared by dissolving 2.0 g of the material to be tested in methyl alcohol and the solution was adjusted to a volume of 100 ml by adding the necessary amount of methyl alcohol.

A 50% solution of 11-cyano-undecanoic acid or its ammonium salt was prepared by dissolving 10 g of the crystal to be tested in 10 ml of acetic acid.

The absorbance (As) of the solution of 11-cyano-undecanoic acid or its ammonium salt to be tested was measured by the same method as that for the standard Hazen solution. The Hazen number of the 2% or 50% solution, or other solution containing 11-cyano-undecanoic acid therein, was determined in accordance with the following equation:

$$\text{Hazen number} = A_s \times (500/0.674)$$

EXAMPLE 1

A crude oily material containing 11-cyano-undecanoic acid therein was produced by thermally decomposing 1,1'-peroxy-dicyclohexylamine at a temperature of 500° C in accordance with the method disclosed in German Patent Application Laying-open No. 2,038,956, and separating an oily layer containing 11-cyano-undecanoic acid from the thermal cracking product. The crude oily material was dissolved in toluene, and ammonia gas was blown into the solution to convert 11-cyano-undecanoic acid into its ammonia salt. The ammonium salt was crystallized, and recovered from the solution. The resultant crude crystals of the ammonium salt of 11-cyano-undecanoic acid were subjected to a purifying process without convertion of the ammonium salt into the free acid. The crude crystals contained 95.1% by weight of 11-cyano-undecanoic acid and had a 2% solution Hazen number of 33. 260 g of the crude crystals were mixed into 1400 g of a solvent mixture consisting of 45% by weight of acetic acid and 55% by weight of water, and the mixture was heated to a temperature of 45° C to uniformly dissolve the crude crystals. A refining gas consisting of oxygen containing therein 1.32% by volume of ozone was directly blown into the solution at the above-mentioned temperature at a flow rate of 1 liter/minute for 96 minutes. That is, the ozone was used in an amount of 0.97% based on the weight of the crude crystals used. Using the ozone-refining process, the solution became colorless, because the colored substances in the crystals were completely decolorized. The solution was cooled to a temperature of 18° C to crystallize the pure 11-cyano-undecanoic acid. The resultant crystals were separated from the solution by way of suction filtration, washed with 300 ml of water and, then, dried. Colorless crystals of the purified 11-cyano-undecanoic acid were obtained in an amount of 236.3 g in a recovery yield of 95.3%. The crystals contained 99.7% by weight of pure 11-cyano-undecanoic acid and had a 50% solution Hazen number of 22.

EXAMPLE 2

Crude crystals of ammonium salt of 11-cyano-undecanoic acid containing 95.7% by weight of 11-cyano-undecanoic acid and a relatively large amount of coloring substances and having a 2% solution Hazen number of 230 which have been prepared by the same method as in Example 1, were purified by the following method.

70 g of the crude crystals were dissolved in 350 g of a solvent mixture consisting of 45% by weight of acetic acid and 55% by weight of water at a temperature of 45° C. 2 g of activated carbon were dispersed into the solution and the dispersion was stirred for 30 minutes and filtered at a temperature of 45° C to preliminarily decolorize the solution. By the preliminary decoloration, the Hazen number of the solution was decreased from 2480 before the preliminary decoloration to 1100 thereafter. When the solution was cooled to a temperature of 8° C to crystallize the preliminarily decolorized 11-cyano-undecanoic acid, the resultant crystals had a 50% solution Hazen number of 480. This large Hazen number means that the preliminarily decolorized solution still contained therein a relatively large amount of the colored substances. When the activated carbon was used in an amount of 8 g, which was 4 times that of the 2 g of activated carbon initially used, the resultant crystals had a 50% solution Hazen number of 360. This indicated that there was not a remarkable improvement in the decoloration of the crude crystals by increasing the amount of activated carbon to be added into the solution of the crude crystals.

A refining gas consisting of oxygen gas containing therein 2.17% by volume of ozone was directly blown into the solution which had been preliminarily decolorized by 2 g of activated carbon, at a temperature of 45° C at a flow rate of 300 ml/minutes for 160 minutes. By this refining, the Hazen number of the solution was decreased from 1040 to 72. This indicated that the solution was substantially completely decolorized. The amount of ozone used in the above process was 1.1% based on the weight of the crude crystals.

After completion of the ozone refining process, the solution was cooled to a temperature of 5.5° C, to crystallize the purified 11-cyano-undecanoic acid. The resultant crystals were separated from the solution by suction filtering, washed with 200 ml of water and dried. 65.6 g of colorless crystals were obtained in a recovery yield of 97.7%. The resultant purified 11-cyano-undecanoic acid has a purity of 99.8% by weight and a 50% solution Hazen number of 33.

EXAMPLE 3

Crude crystals of ammonium salt of 11-cyano-undecanoic acid containing therein 95.5% by weight of 11-cyano-undecanoic acid and having a 2% solution Hazen number of 190, were recovered from a thermal decomposing product from 1, 1'-peroxy-dicyclohexylamine by the same method as in Example 1. 100 g of the crude crystals were dissolved into 375 g of a solvent mixture consisting of 40% by weight of propionic acid and 60% by weight of water at a temperature of 45° C. A refining gas consisting of oxygen gas containing therein 0.66% by volume of ozone was directly blown into the solution at a flow rate of 2 liters/minute and a temperature of 45° C, for 1 hour. The solution was, thereafter, cooled to a temperature of 6° C to crystallize the purified 11-cyano-undecanoic acid from the solution. The crystals were separated by suction filtration from the solution, washed with 200 ml of water and, then, dried. 92.1 g of colorless crystals having a purity of 11-cyano-undecanoic acid of 99.6% by weight and a 50% solution Hazen number of 42 were obtained in a recovery yield of 96.1%.

EXAMPLE 4

Crude crystals of ammonium salt of 11-cyano-undecanoic acid containing 90.5% by weight of 11-cyano-undecanoic acid and having a 2% solution Hazen number of 140, were prepared by crystallizing the crude ammonium salt from an aqueous ammonia solution of a crude oil obtained from the thermal decomposing product which had been produced from 1, 1'-peroxy-dicyclohexylamine, in accordance with the method disclosed in British Pat. No. 1,266,213.

70 g of the crude crystals were purified in accordance with the same method as in Example 2. 62.1 g of the purified crystals were obtained in a recovery yield of 98.0%. The purified crystals of 11-cyano-undecanoic acid had a purity of 99.8% by weight and a 50% solution Hazen number of 20.

For comparison, 70 g of the same crude crystals as used above were dissolved in 420 g of an aqueous solution of 6.5% by weight of ammonia at a temperature of 45° C. In accordance with the same method as in Example 2, 2 g of activated carbon were added to the solution in order to decolorize the solution. The solution was filtered to remove the activated carbon, cooled to a temperature of 5° C and maintained at that temperature for 1 night in order to crystallize the decolorized ammonium salt. The slurry formed above was filtered to separate the decolorized crystals from the solution. The crystals thus separated were washed with 200 ml of a diluted aqueous ammonia solution and, then, dried. 57.3 g of the decolorized crystals of ammonium salt of 11-cyano-undecanoic acid, containing 93.3% by weight of 11-cyano-undecanoic acid and having a 50% solution Hazen number of 160, were obtained in a recovery yield of 84.4%.

What we claim is:

1. A method for purifying 11-cyano-undecanoic acid, comprising the steps of:
   preparing a solution of a crude 11-cyano-undecanoic acid in the form of free acid or its ammonium salt in a solvent mixture consisting of acetic acid or propionic acid and water in a mix ratio by weight of 1 : 0.05 to 3 respectively;
   bringing a refining gas containing 0.1–5% by volume of ozone into contact with said solution at a temperature of 15° to 100° C;
   crystallizing said 11-cyano-undecanoic acid from said solvent mixture, and;
   separating the resulting crystals of 11-cyano-undecanoic acid from said solution at a temperature of 5° to 25° C.

2. A method as claimed in claim 1, wherein said crude 11-cyano-undecanoic acid is recovered from a crude oily material which has been prepared by thermally cracking 1, 1'-peroxy-dicyclohexylamine at a temperature of 300° to 1000° C.

3. A method as claimed in claim 1, wherein said crude 11-cyano-undecanoic acid has a 2% solution Hazen number of 3000 or less.

4. A method as claimed in claim 3, wherein said 2% solution Hazen number of said crude 11-cyano-undecanoic acid is 1000 or less.

5. A method as claimed in claim 1, wherein said mixing ratio of acetic acid or propionic acid to water in said mixture solvent is 1 : 0.5 to 2 respectively.

6. A method as claimed in claim 1, wherein said ozone contact temperature is 15° to 60° C.

7. A method as claimed in claim 1, wherein said ozone is used in an amount of 0.05 to 5% based on the weight of said crude 11-cyano-undecanoic acid.

8. A method as claimed in claim 1, wherein said crude 11-cyano-undecanoic acid solution is preliminarily brought into contact with activated carbon.

* * * * *